United States Patent
Fiedler et al.

(10) Patent No.: US 6,752,778 B1
(45) Date of Patent: Jun. 22, 2004

(54) REMOVAL OF WASTE PRODUCTS BY SUCTION DURING THE ABLATION OF BIOLOGICAL TISSUE

(75) Inventors: Joachim Fiedler, Crailsheim (DE); Claus Goder, Nuremberg (DE); Eckhard Schroeder, Ecktenal (DE); Bernhard Seitz, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 39 days.

(21) Appl. No.: 09/762,498

(22) PCT Filed: Jun. 3, 2000

(86) PCT No.: PCT/EP00/05079
§ 371 (c)(1),
(2), (4) Date: Apr. 26, 2001

(87) PCT Pub. No.: WO00/74581
PCT Pub. Date: Dec. 14, 2000

(30) Foreign Application Priority Data

Jun. 7, 1999 (DE) .......................................... 199 27 016
Apr. 25, 2000 (DE) .......................................... 100 20 522

(51) Int. Cl.$^7$ ........................... A61M 37/00; A61M 1/00
(52) U.S. Cl. ......................................... 604/23; 604/315
(58) Field of Search ................................ 604/290, 313, 604/315, 23, 27, 28

(56) References Cited

U.S. PATENT DOCUMENTS

| 5,015,243 A | * | 5/1991 | Schifano ..................... 604/315 |
| 5,108,389 A | | 4/1992 | Cosmescu |
| 5,156,618 A | * | 10/1992 | Fiore et al. ................. 604/315 |
| 5,181,916 A | * | 1/1993 | Reynolds et al. ............. 604/22 |
| 5,199,944 A | * | 4/1993 | Cosmescu ..................... 600/560 |
| 5,279,599 A | * | 1/1994 | Wilk .......................... 604/313 |
| 5,336,218 A | * | 8/1994 | Linhares ..................... 600/560 |
| 5,344,418 A | | 9/1994 | Ghaffari |
| 5,409,484 A | * | 4/1995 | Erlich et al. ................ 128/897 |
| 5,441,482 A | * | 8/1995 | Clague et al. .............. 261/79.2 |
| 5,616,139 A | | 4/1997 | Okamoto |
| 5,626,568 A | | 5/1997 | Yeh et al. |
| 5,630,807 A | | 5/1997 | Joffe |
| 5,941,873 A | * | 8/1999 | Korenfeld ..................... 604/313 |
| 6,146,353 A | * | 11/2000 | Platt, Jr. ...................... 604/22 |

FOREIGN PATENT DOCUMENTS

| DE | 197 27 573 | 5/1998 |
| DE | 197 10 676 | 9/1998 |
| EP | 0 412 789 | 2/1991 |

* cited by examiner

Primary Examiner—Weilun Lo
Assistant Examiner—C Anderson
(74) Attorney, Agent, or Firm—Reed Smith LLP

(57) ABSTRACT

A arrangement and processes is disclosed for the suction removal of waste products such as smoke and tissue particles in the ablation of biological tissue by means of a laser beam, wherein the laser beam is directed to the tissue through the orifice of a tubular channel and the waste products are sucked through the orifice into the channel. It is provided in an arrangement of the type mentioned above that the inner wall of the channel has at least one outlet opening for a gas in the vicinity of the orifice and the flow of gas is directed to the center of the channel and therefore toward the laser beam. In this way, it is effectively achieved that the gas does not flow through between the orifice and the treatment area so as to flow over the surface of the substance, but exits already from the orifice or from the immediate vicinity of the orifice under by suitable pressure and is guided into the interior of the channel.

9 Claims, 2 Drawing Sheets

REMOVAL OF WASTE PRODUCTS BY SUCTION DURING THE ABLATION OF BIOLOGICAL TISSUE

BACKGROUND OF THE INVENTION

1. Field of the Invention

The invention is directed to an arrangement for the suction removal of waste products such as smoke and tissue particles in the ablation of biological tissue by means of laser radiation, wherein the laser radiation is directed to the tissue through the orifice of a tubular channel and the waste products are sucked through the orifice into the channel.

2. Description of Related Art

The removal of biological tissue by application of laser energy without thermal injury to the target areas is known. This semi-nonthermal process is used, for example, in medicine for cutting cartilage, hard tooth tissue, and skin areas as well as in ophthalmic surgery for shaping the cornea (photorefractive keratectomy). Processes of this kind and the associated equipment are disclosed, for example, in DE 197 27 573 C1 and EP 0 412 789 B1.

It is disadvantageous that waste products in the form of smoke or tissue particles occurring during the removal of tissue impair the air quality in the immediate vicinity of the treatment site resulting, on the one hand, in noxious odor for the patient and treating personnel and, on the other hand, in partial weakening of the laser radiation. The latter is especially significant in photorefractive keratectomy in which the surface of the cornea is shaped by precise removal of material. In this case, apart from the ability to direct the laser beam in an unimpeded and precise manner, it is also important that the radiation energy is introduced into the cornea with exactly constant intensity, so that the results of ablation can be achieved with the desired quality. However, the intensity is influenced by escaping smoke clouds and tissue particles crossing the laser beam, which can lead to irregular and therefor unwanted changes in ablation.

U.S. Pat. No. 5,344,418 describes an arrangement in which an applicator has flow channels for gases or air near the outlet opening for the laser beam, a flow of gas or air being directed from these flow channels to the treated tissue during treatment, which has the intended result that the troublesome ablated waste products are blown away from the treatment area.

Apart from the fact that this does not solve the problem of air contamination and noxious odor for the patient and operator, another disadvantage consists in that the air flow occurring relative to the surface of the treated biological substance disadvantageously leads to a drying out of this substance. This drying causes unpredictable and often excessive ablation.

The disadvantages mentioned above are also not overcome by the solution disclosed in U.S. Pat. No. 5,181,916. In this case, impurities are not blown away by the gas flow is directed to the treated area; rather, the smoke gases occurring at the treatment site are sucked off by means of the gas flow. A suction opening which is arranged concentrically about the orifice and through which the laser beam exits is used for this purpose. Because of the gas flowing away over the tissue, the tissue is also dried up in this case.

OBJECT AND SUMMARY OF THE INVENTION

Proceeding from this prior art, it is the primary object of the invention to reduce unwanted variations in laser radiation intensity could by ablation waste products while retaining the advantages of the elimination of ablation waste products by suction removal and also to avoid as far as possible drying out the treated substance.

According to the invention, in an arrangement of the type mentioned above, the inner wall of the channel has at least one outlet opening for a gas in the vicinity of the orifice and the flow of gas is directed to the center of the channel.

Further, in an arrangement of the type mentioned above, the inner wall of the channel has at least one outlet opening for a gas in the vicinity of the orifice, wherein the flow of gas is directed from the outlet opening substantially opposite to the radiating direction of the laser beam into the channel.

In a particularly preferred construction of the invention, the tubular channel has a portion which tapers conically toward the orifice.

Further, it lies within the scope of this invention that the tubular channel has, at least in the conically extending portion, two chambers extending concentrically around its circumference, one of which chambers is provided for guiding gas to the outlet opening. The second chamber is used for carrying the gas, which is sucked off and which entrains the waste products, out of the channel interior. For this purpose, the second chamber is connected with the channel interior by a suction opening on the one hand and is connected with a suction device via a suction line on the other hand.

It is effectively achieved by means of this arrangement that the gas does not flow through between the orifice and the treatment area so as to flow over the surface of the substance, but exits already from the orifice or from the immediate vicinity of the orifice accompanied by suitable pressure and is guided into the interior of the channel.

In this way, the underpressure or vacuum formed by the suction is predominantly or even completely balanced by the gas volume guided out through the outlet openings, with the result tat there is only a slight flow of air, if any, outside the channel, particularly between the orifice and the substance surface, and drying out can accordingly no longer occur.

The smoke occurring during treatment and coming from the treatment site and the tissue particles detaching from the latter move in the direction of the orifice, are acquired by the flow of gas or air within the tubular channel, and are carried off.

In advantageous constructions, outlet openings arranged in a radially symmetric manner about the center of the channel or, alternatively, an annularly extending outlet opening can be provided, for example. Both variants achieve comparable gas flow which is initially directed from the outlet openings into the mouth toward the center of the channel and then, due to the vacuum formed in the channel interior, is deflected opposite the direction of the laser beam into the channel.

The outlet openings are preferably expanded in the manner of a diffusor, so that the gas exits from these outlet openings with decreasing flow velocity and unwanted eddying of the gas flow is accordingly prevented. Above all, the gas exiting from the outlet openings is prevented from moving toward the treatment area due to eddying or excessive flow velocity out of the orifice.

In a particularly preferred construction of the invention, air is provided as gas and the outlet openings are connected with an air compressor or with a pressure vessel filled with air. Means for regulating the pressure of the supplied air and therefore also the flow velocity should advantageously be provided at the air compressor or at the pressure vessel. Such means e.g., pressure reducing valves, are sufficiently known in the prior art and need not be described in more detail.

Further, it can advantageously be provided that the inner wall of the channel has a plurality of suction openings arranged in a radial symmetric manner about the center of the channel and which communicate with a suction device. This arrangement also prevents a whirling of the air which exits from the outlet openings and is directed to the suction openings and carries the smoke gases and tissue particles, since it always only needs to travel a very short route between the outlet opening and suction opening.

The air flow takes place substantially close to the inner wall of the channel, while the center which is reserved for the laser beam is impaired only slightly by the air flow. Also, as a result of this, the smoke gas and tissue particles move and are discharged with the air flow extensively outside the laser beam, so that the energy impinging on the treatment area is not impaired in intensity by opaque particles or, if so, only to a substantially smaller extent than in the prior art.

It is further preferably provided that the total cross section of the outlet openings and the total cross section of the suction openings, the overpressure at the outlet openings and the vacuum at the suction openings as well as the flow velocities in the outlet openings and the flow velocities in the suction openings are adapted to one another in such a way that the quantity of air sucked off per time unit is greater than the quantity of air guided through the outlet openings by a factor between 1.1 and 1.3.

In this way, it is ensured that the supplied quantity of air is somewhat smaller than the quantity of air sucked off and is therefore not sufficient to replace the quantity of air that is sucked out in such a way as to balance pressure, so that a quantity of air corresponding to the difference is sucked into the channel in addition from the outside through the orifice. This results in a slight air flow close to and outside of the orifice which serves to intercept the smoke gas and tissue particles rising from the treatment site and suck them into the annular channel. This factor and therefore the quantity of air sucked in from outside of the channel can be regulated by means which are provided for influencing the pressure of the supplied air and for influencing the flow velocity of the supplied air.

By means of the arrangement according to the invention, it is achieved in an extremely effective manner that the noxious odor for patient and treating physician is eliminated, the energy density of the laser radiation remains substantially uniform over the period of operation by removing smoke gases and tissue particles, and air flows are also kept away from the treatment area to a great extent.

In another preferred construction of the invention, a device can be provided for alternately interrupting the laser radiation impinging on the tissue on the one hand and the air flow on the other hand. In this way, a treatment phase in which the laser radiation was directed to the tissue and a partial ablation is carried out is advantageously followed by a suction phase in which air is supplied and sucked out in the manner described above and the ablation products are carried away. At the conclusion of this "cleaning phase", the air flow is interrupted and a new treatment phase takes place. It is also achieved in this way that the ablation products are sucked away so that there is no noxious odor and the laser radiation is also kept free of opaque particles, so that radiation with uniform energy density can impinge on the tissue.

Finally, it can also be provided in another arrangement that the channel is arranged so as to be swivelable relative to the laser beam, wherein the laser beam is enclosed by the channel in a preferred orientation of the channel. Accordingly, it is possible for the treating physician, for example, to swivel the tubular channel toward the side for phases of the treatment requiring a better view of the treatment area.

The invention is further directed to a process for ablation of biological tissue by means of laser radiation, preferably for purposes of changing the shape of the lenses of the eyes for correction of defective vision. According to the invention, the waste products occurring during removal of material, such as smoke and tissue particles, are removed from the treatment site by a gas flow or air flow without affecting the intensity of the laser radiation.

The waste products are advantageously removed by a gas flow or air flow which is not directed to the treated tissue and which does not flow over the tissue or, if so, only to a slight extent, in order to prevent drying out of the tissue.

In an arrangement of the process according to the invention, it is provided that initially a portion of the total tissue to be removed is removed, the treatment is then interrupted and the air which is located in the radiating direction of the laser beam and which includes waste products such as smoke and tissue particles is sucked out during the interruption and replaced by air that is not contaminated by waste products, whereupon treatment proceeds.

Several such partial treatments can advantageously be carried out and, between these partial treatments, the air with impurities can be sucked away and these process steps are alternately repeated until the tissue removal is completed.

The laser shot positions to be selected for each partial correction are preferably selected and predetermined according to Patent DE 197 27 573.

The process according to the invention has the advantage that during the individual partial corrections there is only a slight impairment of the laser beam by the ablated waste products which continually occur. An uneven treatment of the surface due to variations in the intensity of the laser radiation and the resulting uneven removal of material are accordingly prevented.

BRIEF DESCRIPTION OF THE DRAWINGS

The invention will be described more fully in the following with reference to two embodiment examples. In the accompanying drawings.

DESCRIPTION OF THE PREFERRED EMBODIMENTS

Figure 1:
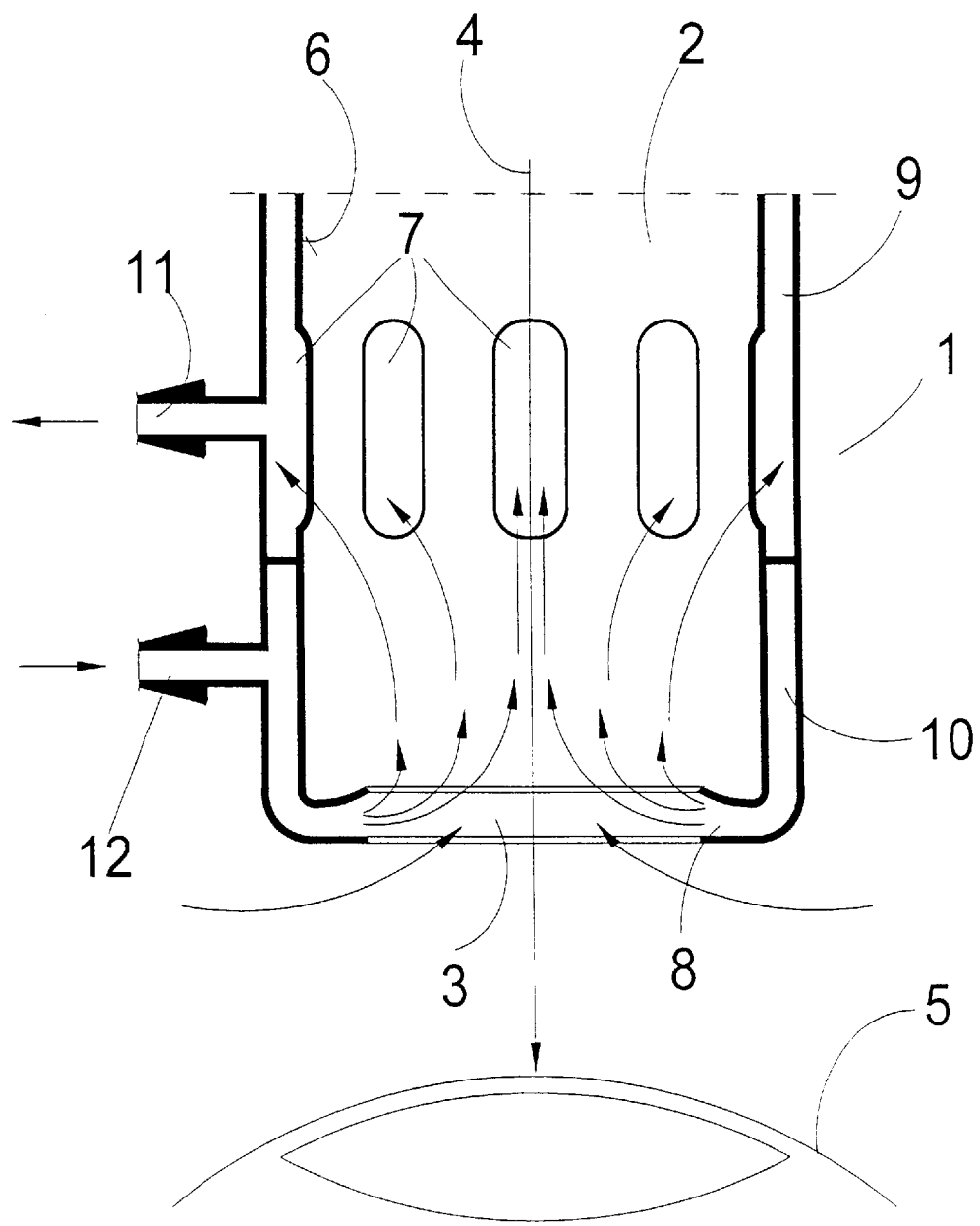
FIG. 1 shows a schematic view of the invention in a first embodiment example in which the orifice has an outlet opening for a gas, wherein the flow direction of the gas is directed to the center of the channel.

The drawings show the mouthpiece 1 of a device which is used, for example, for photorefractive keratectomy in which the curvature of the cornea of the eye is corrected by targeted, partial removal of material by the action of laser radiation. The mouthpiece 1 substantially comprises a tubular channel 2, a laser beam 4 being directed to the cornea 5 through its orifice 3.

Smoke gas is formed during this treatment and ablated tissue particles also issue from the treated site at the cornea 5.

In order to prevent smoke gas and tissue particles from residing temporarily in the laser beam and, as opaque particles, reducing the energy density radiating into the cornea 5, a plurality of suction openings 7 are arranged in the inner wall 6 of the channel 2 in a radially symmetric manner about the center of the channel in which the laser beam 4 preferably travels. The suction openings 7 communicate with a suction opening which generates a vacuum so that air is sucked out of the inside of the channel through the suction openings 7 and the smoke gas and tissue particles jumping off of the cornea 5 are carried off with this sucked out air.

Further, to prevent the air which flows out due to the pressure equilibrium from drying out the location to be treated on the cornea 5 and to prevent the smoke gas and the released tissue particles from entering or remaining too long in the laser beam 4, at least one outlet opening 8 for air is provided, according to the invention, in the orifice 3.

The outlet opening 8 is formed annularly and is arranged centric to the center of the channel. The outlet opening 8 is directed to the center of the channel and is shaped in such a way that its cross section widens in the direction of flow, so that the flow velocity of the air flowing toward the center of the channel is reduced.

It can also be seen from the drawing that the mouthpiece 1 is constructed as a double-walled pipe with chambers 9 and 10 which are separate from one another. Chamber 9 communicates with a connection piece 11 and chamber 10 communicates with a connection piece 12. The connection pieces 11, 12 are constructed as hose connections, for example, and can accordingly be connected, via hoses, with a suction device (referring to chamber 9 and connection piece 11 in the example), with a compressor, or with a compressed-air tank (referring to chamber 10 and connection piece 12 in the example).

With corresponding means, known per se, for regulating air flows, the quantity of air supplied through the connection piece 12 and the quantity of air guided through connection piece 11 can be adapted to one another in such a way that the supplied quantity of air is sufficient to compensate for the vacuum generated by the quantity of air guided out so as to prevent the formation of an air flow in the area between the orifice 3 and the surface of the cornea 5 by which the vacuum is compensated in the prior art.

In this way, no air movement or only extremely slight air movement occurs in the area between the orifice 3 and the surface of the cornea 5, so that a drying out of the surface of the cornea 5 is prevented.

It also lies within the scope of the invention that the quantity of air that is supplied and the quantity of air that is sucked out are adapted to one another in such a way that the supplied quantity of air is not entirely sufficient to compensate for the suction vacuum, so that air must still flow from the outside through the orifice 3, but without causing excessive air flows or air eddying in the immediate vicinity of the surface of the cornea 5 which would dry out the substance. Although the quantity of air flowing from the outside is small, it reinforces the sucking out of the smoke gas and detached tissue particles occurring during ablation.

The effects and actions mentioned above are achieved, for example, when the orifice 3 has a diameter of approximately 40 mm and the distance between the orifice 3 and the surface of the treatment area is about 50 mm. An air volume of 40 liters per minute should flow out of the outlet opening 8. The sucked out air quantity should be between 40 and 55 liters in the same unit of time.

Figure 2:
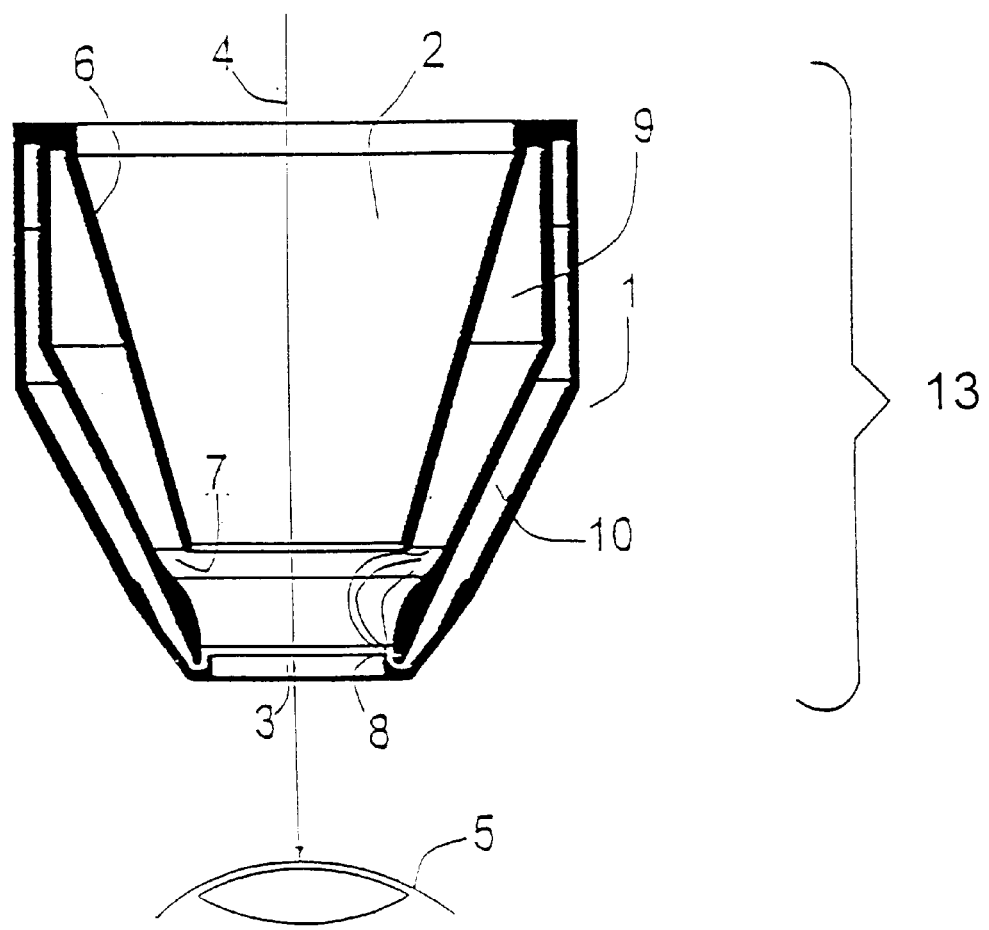
FIG. 2 shows a schematic view of the gas in a second embodiment example in which the orifice likewise has an outlet opening for a gas, but the flow direction of the gas is directed into the channel substantially opposite to the radiation of the laser beam.

FIG. 2 shows another embodiment example of an arrangement, according to the invention, for sucking out waste products in the ablation of biological tissue.

In this case, the tubular channel 2 likewise has an orifice 3 and an outlet opening 8 is provided in its vicinity. The special feature in this case consists in that the flow direction of the gas from the outlet opening 8 is directed substantially opposite to the radiating direction of the laser beam 4 into the channel 2. It is effectively achieved in this way that the gas does not flow through the free space between the orifice 3 and the cornea 5 so as to flow over the surface of the cornea and dry it out, but rather is deflected into the interior of the channel when exiting from the outlet opening 8. The pressure ratios are adapted in the manner described above.

Accordingly, it is achieved in a particularly advantageous manner that the ablation products are sucked out without substantially impairing the intensity of the laser radiation.

FIG. 2 further shows that the tubular channel 2 has a conically extending portion (13) in this case. In this case, also, as in the embodiment example described above, the mouthpiece 1 is provided with chambers 9 and 10 which are separated from one another and which extend concentrically about the circumference. One of the chambers (10) is provided for supplying gas to the outlet opening (8) and the second chamber (9) is provided for discharging the sucked off gas, including the waste products.

For this purpose, the chambers 9, 10 communicate with connection pieces (not shown here) which are constructed, for example, as hose connections and are connected, via hoses, with a suction device (referring to chamber 9), with a compressor or a compressed-air tank (referring to chamber 10).

While the foregoing description and drawings represent the present invention, it will be obvious to those skilled in the art that various changes may be made therein without departing from the true spirit and cope of the present invention.

What is claimed is:

1. An arrangement for the suction removal of waste products including smoke and tissue particles in the ablation of biological tissue by laser radiation, comprising:
   a tubular channel having an orifice through which laser radiation is directed to the tissue and through which waste products are sucked into the tubular channel;
   the tubular channel having an inner wall which has at least one outlet opening for a gas in a vicinity of the orifice and wherein flow of gas is directed to the center of the tubular channel;
   wherein an outlet opening is provided which extends annularly;
   wherein the outlet opening are widened to produce a diffusion effect.

2. The arrangement for the suction removal of waste products according to claim 1, wherein the inner wall of the tubular channel has at least one outlet opening for a gas in the vicinity of the orifice, wherein the flow of gas is directed from the outlet opening substantially opposite to a radiating direction of the laser radiation into the tubular channel.

3. The arrangement according to claim 1, wherein the tubular channel has a portion which tapers conically toward the orifice.

4. The arrangement according to claim 3, wherein the tubular channel has, at least in a conically extending portion, two chambers extending concentrically around its circumference, one of said chambers being provided for guiding gas to the outlet opening, and a second chamber being used for carrying away the sucked up gas, including the waste products.

5. The arrangement according to claim 1, wherein a plurality of outlet openings are provided and are arranged in a radial symmetric manner about the center of the tubular channel.

6. The arrangement according to claim 1, wherein air is provided as gas and an outlet openings are connected with a compressor or with a pressure vessel filled with air.

7. The arrangement according to claim 1, wherein a device is provided for alternately interrupting the laser radiation impinging on the tissue and the supply and suction of air.

8. The arrangement according to claim 1, wherein the channel is arranged so as to be swivelable relative to the laser radiation, wherein the laser radiation is a laser beam is enclosed by the channel in a preferred orientation of the tubular channel.

9. An arrangement for the suction removal of waste products including smoke and tissue particles in the ablation of biological tissue by laser radiation, comprising:

a tubular channel having an orifice through which laser radiation is directed to the tissue and through which waste products are sucked into the tubular channel;

the tubular channel having an inner wall which has at least one outlet opening for a gas in a vicinity of the orifice and wherein flow of gas is directed to the center of the tubular channel wherein the inner wall of the channel has a plurality of suction openings arranged in a radial symmetric manner about the center of the channel and which communicate with a suction device;

wherein annular openings are provided and wherein the total cross section of outlet openings and the total cross section of the suction openings are structured so that the overpressure at the outlet openings and the vacuum at the suction openings, as well as the flow velocities in the outlet openings and the flow velocities in the suction openings are structured relative to one another in such a way that a first quality of air sucked off a defined area on an eye per time unit is greater than a second quantity of air guided through the outlet openings by a factor between 1.1 and 1.3.

\* \* \* \* \*